US00PP13308P2

(12) United States Plant Patent
Cascante

(10) Patent No.: US PP13,308 P2
(45) Date of Patent: Dec. 3, 2002

(54) DOUBLE IMPATIENS PLANT NAMED 'CAMEO PINK SURPRISE'

(75) Inventor: Xenia Cascante, Alajuela (CR)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 09/876,931

(22) Filed: Jun. 11, 2001

(51) Int. Cl.[7] ..... A01H 5/00
(52) U.S. Cl. ..... Plt./317

(58) Field of Search ..... Plt./317

*Primary Examiner*—Bruce R. Campell
*Assistant Examiner*—June Hwu
(74) *Attorney, Agent, or Firm*—C. A. Whealy

(57) ABSTRACT

A new and distinct cultivar of Double Impatiens plant named 'Cameo Pink Surprise', characterized by its large pink and white bi-colored flowers; fully double flower form; freely flowering habit with flowers positioned above the foliage; compact, mounded, spreading, densely foliated, and freely branching plant habit; rapid growth rate; and large rounded dark green leaves.

1 Drawing Sheet

BOTANICAL CLASSIFICATION/CULTIVAR DESIGNATION

*Impatiens walleriana* cultivar Cameo Pink Surprise.

BACKGROUND OF THE INVENTION

The present Invention relates to a new and distinct cultivar of Double Impatiens plant, botanically known as *Impatiens walleriana,* and hereinafter referred to by the cultivar name Cameo Pink Surprise.

The new Impatiens is a product of a planned breeding program conducted by the Inventor in Cartago, Costa Rica. The objective of the breeding program was to develop new compact Double Impatiens cultivars with large fully double flowers, excellent branching, and interesting flower and foliage colors.

The new Impatiens originated from a cross made by the Inventor of a proprietary selection of *Impatiens walleriana* identified as code number 88VAR121A, not patented, as the female, or seed parent, with a proprietary selection of *Impatiens walleriana* identified as code number F2 (PK:DB), as the male, or pollen parent. The cultivar Cameo Pink Surprise was discovered and selected by the Inventor as a flowering plant within the progeny of the stated cross in a controlled environment in Cartago, Costa Rica.

Asexual reproduction of the new cultivar by terminal cuttings taken at Cartago, Costa Rica, has shown that the unique features of this new Impatiens are stable and reproduced true to type in successive generations of asexual reproduction.

SUMMARY OF THE INVENTION

The following traits have been repeatedly observed and are determined to be the unique characteristics of 'Cameo Pink Surprise'. These characteristics in combination distinguish 'Cameo Pink Surprise' as a new and distinct cultivar:

1. Large pink and white bi-colored flowers.
2. Fully double flower form.
3. Freely flowering habit.
4. Flowers positioned above the foliage.
5. Compact, mounded and spreading plant habit.

6. Rapid growth rate.
7. Freely branching habit.
8. Large rounded dark green leaves; densely foliated.

In side-by-side comparisons conducted in Cartago, Costa Rica, plants of the new Impatiens differ from plants of the female parent, the selection 88VAR121A, in the following characteristics:

1. Leaves of plants of the new Impatiens are larger and more rounded than leaves of plants of the selection 88VAR121A.
2. Plants of the new Impatiens have larger flowers than plants of the selection 88VAR121A.
3. Plants of the new Impatiens have fully double flowers whereas plants of the selection 88VAR121A have single flowers.
4. Flowers of plants of the new Impatiens are sterile whereas flowers of plants of the selection 88VAR121A are fertile.

In side-by-side comparisons conducted in Cartago, Costa Rica, plants of the new Impatiens differ from plants of the male parent, the selection F2 (PK:DB), in the following characteristics:

1. Plants of the new Impatiens are more compact and more mounded than plants of the selection F2 (PK:DB).
2. Plants of the new Impatiens have larger flowers than plants of the selection F2 (PK:DB).
3. Flowers of plants of the new Impatiens are pink and white bi-colored whereas flowers of plants of the selection F2 (PK:DB) are solid pink in color.
4. Flowers of plants of the new Impatiens are sterile whereas flowers of plants of the selection F2 (PK:DB) are fertile.

The new Impatiens can be compared to the *Impatiens walleriana* cultivar Sparkler Rose, disclosed in U.S. Plant Pat. No. 9,603. However, in side-by-side comparisons conducted in Lompoc, Calif., plants of the new Impatiens differ from plants of the cultivar Sparkler Rose in the following characteristics:

1. Plants of the new Impatiens are more mounded and spreading than plants of the cultivar Sparkler Rose which are more upright in plant habit.

2. Stems of plants of the new Impatiens are red purple in color whereas stems of plants of the cultivar Sparkler Rose are yellow green in color.

3. Plants of the new Impatiens have larger flowers than plants of the cultivar Sparkler Rose.

4. Flowers of plants of the new Impatiens are lighter pink in color than flowers of plants of the cultivar Sparkler Rose.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens.

The photograph comprises a top perspective view of a typical hanging basket container of 'Cameo Pink Surprise' with three plants per container about 10 weeks after planting rooted cuttings.

DETAILED BOTANICAL DESCRIPTION

The cultivar Cameo Pink Surprise has not been observed under all possible environmental conditions. The phenotype may vary somewhat with variations in environment such as temperature, light intensity, daylength, water status, and fertilizer types and rate without, however, any variance in genotype. The following observations, measurements and comparisons describe plants grown in Lompoc, Calif., under commercial practice in a fiberglass-covered greenhouse with day temperatures about 21 to 24° C., night temperatures about 16 to 18° C. and light levels generally about 3,000 to 4,000 footcandles. Three rooted cuttings were planted in 20-cm hanging basket containers and grown for about 8 to 10 weeks.

In the following description, color references are made to The Royal Horticultural Society Colour Chart except where general terms of ordinary dictionary significance are used.

Botanical classification: *Impatiens walleriana* cultivar Cameo Pink Surprise.

Parentage:

*Female parent*.—Proprietary selection of *Impatiens walleriana* identified as code number 88VAR121A, not patented.

*Male parent*.—Proprietary selection of *Impatiens walleriana* identified as code number F2 (PK:DB), not patented.

Propagation:

*Type cutting*.—Terminal cuttings.

*Time to initiate roots*.—Summer: About 10 days at 21° C. Winter: About 12 days at 21° C.

*Time to produce a rooted cutting*.—Summer and winter: About 28 days at 21° C.

*Root description*.—Numerous, fibrous, fine and freely branching.

Plant description:

*General appearance*.—Compact, mounded and spreading. Appropriate for 10 to 15-cm pots and 20 and 25-cm hanging basket containers.

*Growth and branching habit*.—Vigorous and freely-branching with at least ten lateral branches at the base, dense and bushy growth. Pinching, that is, removal of the terminal apices, is typically not required.

*Crop time*.—Rapid growth rate. From planting one rooted cutting in a 10-cm pot: About 5 to 6 weeks. From planting three rooted cuttings in a 20-cm hanging basket container: About 8 to 10 weeks.

*Plant height*.—About 17 cm.

*Plant spread*.—About 25 cm.

*Lateral branches*.—Length: About 19 cm. Diameter: About 9 mm. Internode length: About 1 to 2 cm. Texture: Smooth, glabrous. Color: 146B heavily overlain with 183D.

*Foliage description*.—Leaves simple, alternate; broad and rounded, generally symmetrical; abundant, densely foliated. Length: About 3.75 cm. Width: About 3.25 cm. Shape: Ovate. Apex: Acute. Base: Acute to rounded. Margin: Slightly serrated to dentate. Texture: Smooth, glabrous. Venation pattern: Pinnate. Color: Young foliage, upper surface: 147B. Young foliage, lower surface: 147C with large, mostly central, irregular areas of 183D. Fully expanded foliage, upper surface: 146A. Fully expanded foliage, lower surface: 146C with large, mostly central, irregular areas of 183D. Venation, upper surface: 146B. Venation, lower surface: 146A. Petiole: Length: About 1.35 cm. Diameter: About 2 mm. Texture: Smooth, glabrous. Color: 183D.

Flower description:

*Flower type and habit*.—Numerous and consistently double pink and white bi-colored flowers. Freely and continuously flowering. Flower buds open similar to a rose in fullness; flowers rounded. Flowers arise from leaf axils. Usually about 8 to 15 flowers and flower buds per lateral branch. Flowers positioned above the foliage and typically face outward to upward. Flowers last about 7 to 10 days on the plant depending on temperature and weather conditions. Flowers not persistent. Flowers not fragrant.

*Flowering season*.—Year-round under greenhouse conditions. In the garden, flowering is continuous from spring until fall.

*Flower size*.—Diameter: About 4.5 cm. Depth: About 2 cm.

*Flower buds*.—Rate of opening: From showing color to fully open flower, about 5 to 7 days is typical depending on temperature. Length: About 1.25 cm. Diameter: About 1 cm. Shape: Ovoid. Flower bud color: 145A; with development, 145A blushed with 55B.

*Petals*.—Quantity/arrangement: About 20 to 25 per flower; imbricate. Length, outer petals: About 2.5 cm. Width, outer petals: About 2.5 cm. Shape: Roughly cordate to ovate. Apex: Rounded or emarginate. Base: Acute. Margin: Entire; slightly ruffled. Texture: Smooth, glabrous. Color: When opening and fully opened, upper surface: Towards margin, pink, 68A; towards center, white, 155C. With subsequent development, pink color becomes lighter, 68B. When opening and fully opened, lower surface: 68B.

*Calyx*.—Number of sepals: Three, one modified into a spur. Sepal shape: Obovate to cordate. Sepal length: About 1 to 2 cm. Sepal width: About 1.2 to 2.5 cm. Sepal color: 145A: towards margins, 55B. Spur: Length: About 3 cm. Color: 146D.

*Peduncles*.—Length: About 2.75 cm. Diameter: Less than 1 mm. Angle: About 45° to the lateral branch. Strength: Strong. Color: 146B heavily overlain with 183D.

*Reproductive organs*.—None observed.

*Seed production*.—Not observed.

Disease resistance: Plants of the new Impatiens have demonstrated good resistance to pathogens common to Impatiens, such as Botrytis.

It is claimed:

1. A new and distinct cultivar of Double Impatiens plant named 'Cameo Pink Surprise', as illustrated and described.

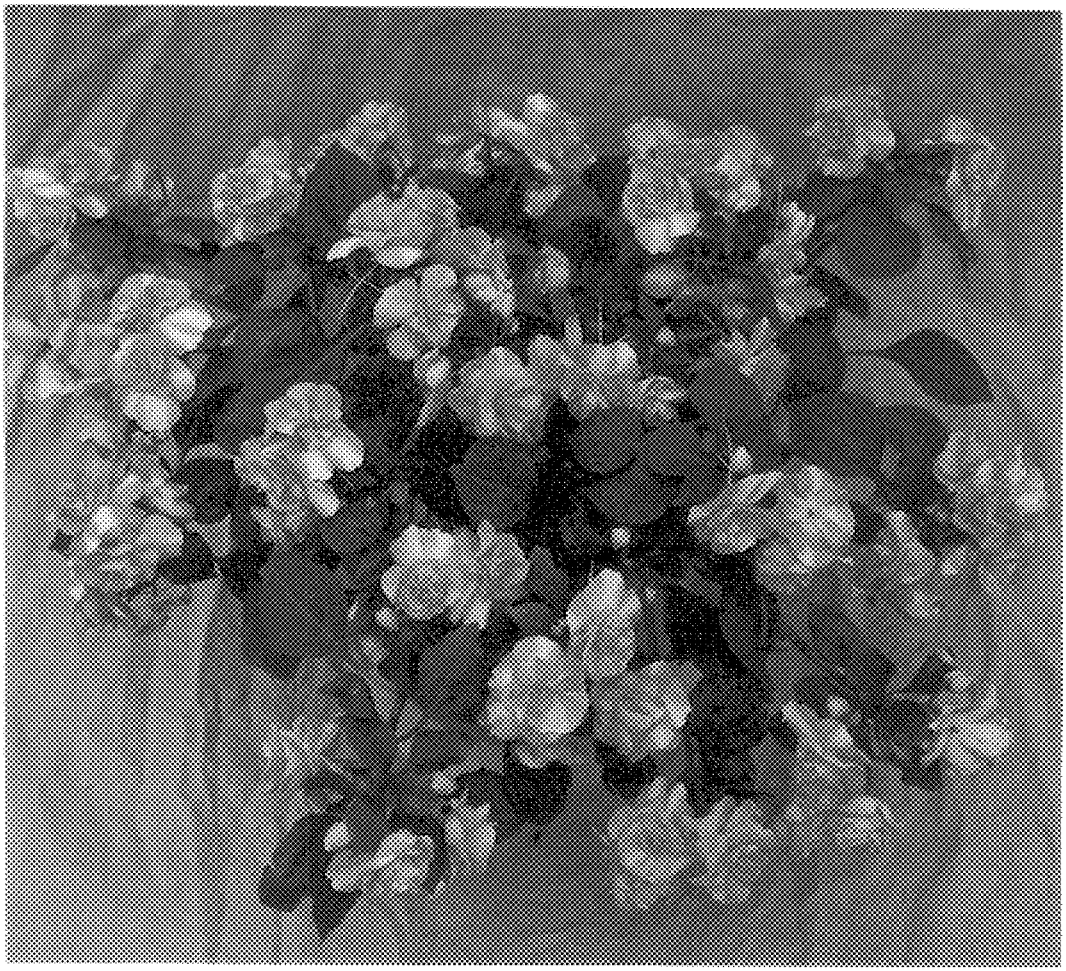

* * * * *